United States Patent

Yokoi et al.

Patent Number: 5,154,747
Date of Patent: Oct. 13, 1992

[54] ANTIFOULING COMPOSITION USING ALKYL-PHENOLS

[75] Inventors: Junji Yokoi, Nara; Akio Harada, Osaka; Kazuo Ina, Shinzuoka, all of Japan

[73] Assignee: Nippon Paint Co., Ltd., Osaka, Japan

[21] Appl. No.: 836,557

[22] Filed: Feb. 18, 1992

Related U.S. Application Data

[63] Continuation of Ser. No. 552,681, Jul. 11, 1990, abandoned.

[30] Foreign Application Priority Data

Jul. 11, 1989 [JP] Japan ............... 1-178458
Mar. 9, 1990 [JP] Japan ............... 2-593440

[51] Int. Cl.$^5$ .................. A01N 31/08; C09D 5/14
[52] U.S. Cl. .................................. 71/67; 71/66; 71/122; 514/717; 514/718; 514/731; 514/738; 106/15.05; 106/18.29
[58] Field of Search .................. 71/66, 67, 122; 514/731, 738, 718, 717; 106/15.05, 18.29

[56] References Cited

U.S. PATENT DOCUMENTS

| 2,192,347 | 2/1937 | Hill et al. ............... 514/731 |
| 2,391,798 | 10/1932 | Read ....................... 514/731 |
| 3,839,212 | 10/1974 | McCoy ..................... 568/607 |

FOREIGN PATENT DOCUMENTS 60-258271 12/1985 Japan.
1525884 9/1978 United Kingdom.

OTHER PUBLICATIONS

Merck Index, 8th ed. p. 746, col. 'nonylphenol' (1968).

Primary Examiner—Richard L. Raymond
Assistant Examiner—B. Bembenick
Attorney, Agent, or Firm—Wenderoth, Lind & Ponack

[57] ABSTRACT

An antifouling composition for use in the control of noxious aquatic life comprising as an active ingredient, one or more phenol derivatives of the formula

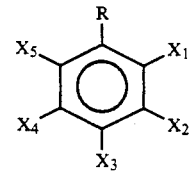

wherein R is a $C_3 \sim C_{21}$ saturated hydrocarbon residue; $X_1 \sim X_5$ each is H, HO or $CH_3O$, providing excluding the case wherein all of $X_1 \sim X_5$ are hydrogen.

This composition is useful as an antifouling paint for marine structures, ships, fishnets, buoys, industrial water system, water cooling system and the like.

1 Claim, No Drawings

ANTIFOULING COMPOSITION USING ALKYL-PHENOLS

This application is a continuation of now abandoned application, Ser. No. 07/552,681 filed Jul. 11, 1990, now abandoned.

FIELD OF THE INVENTION

The present invention relates to an antifouling composition for control of noxious aquatic life, which prevents the attachment and proliferation of such aquatic life on marine structures and industrial water systems.

BACKGROUND OF THE INVENTION

The present invention provides an antifouling composition for use in the prevention of the damages caused by the attachment of fouling creatures to the surfaces of ships, marine structures, fishnets, buoys, sea water conduits and so on, disfunctions of paper mill and other industrial cooling water systems, recycling water cooling systems, etc. due to deposition of slime, or deterioration of the quality of water due to abnormal multiplication of bacteria and other microorganisms.

Marine structures, inclusive of ships, offshore structures, sea water conduit systems of seaside plants, fishnets, culture rafts and buoys, are favorite habitats of large attached animals and plants, such as barnacle, hardshell mussel, sea lettuce (green layer), etc., attached diatom, bacteria and other microorganisms, all of which cause corrosion of structures, increased sea water resistance of slips, clogging of fishnets which may induce a massive death of fish, and increased structure weights which lead to sinking and decreased operation efficiencies. In pipelines for industrial cooling water etc. which utilize natural water such as river or lake water and recycling water cooling systems utilizing city water, bacteria, attached diatom, blue-green algae, pond scum, etc. grow abundantly to cause various troubles such as deterioration of water quality, reduced cooling efficiencies due to attachment of these organisms to the pipe walls, and plugging or reduced flow in the water lines. The slime in the pulping process in a paper mill line causes a serious deterioration of paper quality.

For the purpose of preventing such damages due to harmful aquatic life, chemical control is generally practiced using inorganic heavy metal compounds, organometal compounds, heavy metal salts, inorganic or organic halogen compounds, etc. For example, the bottom plate and sea water inlet of ships and fishnets have heretofore been coated with antifouling paints which are mostly based on organocopper compounds or organotin compounds. In cooling water systems, it is common practice to add an organometal compound, an inorganic or organic halogen compound, a peroxide, or the like either directly or as dissolved or dispersed with a hydrating agent. Such chemical control is often ineffective when the rate of release or dissolution is low and the use of effective concentrations presents toxicity and residue problems which are abhored from the standpoint of environmental hygiene and protection. Therefore, there is a standing demand for an antifouling composition which is free from these safety and environmental risk factors and does not adversely affect the ecosystems and working environments.

OBJECT OF THE INVENTION

The object of the present invention is to provide an antifouling composition which is free from the above-mentioned problems.

SUMMARY OF THE INVENTION

The present invention is directed, in a first aspect, to an antifouling composition comprising, as an active ingredient, one or more phenol derivatives of the general formula

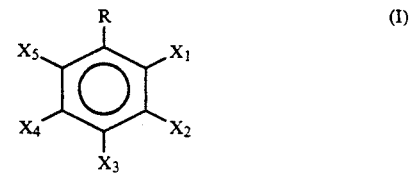

wherein R is a $C_{3-21}$ straight-chain or branched aliphatic saturated hydrocarbon residue; $X_1$ through $X_5$ are the same or different and each is selected from the class consisting of hydrogen, hydroxy and methoxy; provide, however, that all of $X_1$ through $X_5$ cannot be hydrogen.

In a second aspect, the invention is directed to an antifouling composition comprising one or more phenol derivatives of general formula (I) and a water-repellent organic compound as active ingredients.

Phenol is a time-honored disinfectant or preservative which is used generally as an aqueous solution for the disinfection of fingers etc. However, phenol has an irritation odor and is not a satisfactory controlling agent for noxious aquatic organisms. It is not as effective against them as desired, either. On the other hand, alkyl derivatives of phenol are well-known starting materials for synthetic resins etc. but their antifouling effect has never been discussed. The research undertaken by the inventors of this invention revealed that certain phenol derivatives are highly degradable in natural environment, do not cause appreciable residue or accumulation problems and display potent inhibitory activity against sea water bacteria, diatom and other microorganisms and large marine attached life at very low concentration. The antifouling composition of the invention which contains such phenol derivative as an active ingredient exhibits sufficient control activity against aquatic pests at a very low rate of release or dissolution into the water. Thus, in accordance with the invention, one or more of phenol derivatives (I) having a $C_{3-21}$ straight-chain or branched aliphatic saturated hydrocarbon residue are used as the active ingredient for the control of aquatic pests. It has been found that alkylphenols having a hydrocarbon residue of 1 or 2 carbon atoms are not so effective as desired and that alkylphenols having a hydrocarbon residue of too many carbon atoms beyond the abovementioned range must be used in large amounts, thus being economically disadvantageous. The abovedefined phenol derivative of this invention can be made into a solution of, for example, 80% concentration for use as a bath for dipping fishnets or may be incorporated in a coating composition for application as the so-called bottom paint to the ship bottom or underwater structures. The proportion of the phenol derivative in such a coating composition or an antifouling bath for fishnets is generally about 0.5 to 80 weight % and preferably about 1 to 50 weight %. However, the optimum proportion can be selected by reference to the purpose of treatment, desired period of protection, and other factors. Usually, with the phenol derivative (I) in the abovementioned concentration range, the antifouling paint or bath assures a sufficient antifouling effect over a period of more than one year. The formula of such an antifouling paint or bath is optional and the conventional compositions can be selectively utilized. For example, as the resin vehicles for organic solvent-based systems, there may be used vinyl chloride resin, chlorinated rubber-type resin, chlorinated polyethylene resin, chlorinated polypropylene resin, acrylic resin, styrene butadiene resin, polyester resin, epoxy resin, polyamide resin, petroleum resin, silicone resin, silicone rubber-type resin, petroleum wax, paraffin, rosin ester, rosin-type resin, and resins having metal elements, such as tin, copper, zinc, tellurium, etc., in the side chains can be used alone or in combination. For aqueous systems, there may be employed acrylic emulsion resin, epoxy emulsion resin, vinyl acetate resin and so on. Though not essential for antifouling purposes, known antifouling agents may be incorporated as auxiliary antifouling ingredients. In addition, the plasticiers, color pigments, loading pigments, solvents, etc. which are conventionally used may be incorporated in appropriate proportions. Such paints can be manufactured by the per se known technology.

When the antifouling composition is used as dissolved or suspended in a cooling water system or the like, one or more of phenol derivatives of general formula (I) are added to the water system. The concentration of as low as 0.1 to 50 ppm, preferably 0.5 to 30 ppm, of phenol derivative (I) in such a water system is sufficient to produce the required controlling effect. For addition to water systems, the phenol derivative can be directly dissolved or physically suspended, either continuously or intermittently, according to the type of water system to be treated and the status of growth of pest life. The use of phenol derivative (I) in combination with a water-repellent organic compound provides a very effective antifouling composition.

Thus, a sufficient and stable antifouling effect can be achieved by using one or more water-repellent compounds such as silicone oil, vaseline, petroleum wax and liquid paraffin. The marine life attachment inhibition paint previously proposed in Japanese Kokai Patent Publication No. 60-258271/1985 contains a film-forming silicone resin vehicle as an essential ingredient together with an effective amount of a surfactant.

In accordance with the invention, the film-forming silicone resin is not an essential component. Moreover, as apparent if only from its chemical structure, the surface activity of the phenol is by far weaker than the activities of the substances generally called surfactants. Therefore, the use of phenol derivative (I) in combination with a water-repellent organic compound is a novel proposal.

The water-repellent compound to be used in accordance with this invention is one or more members of silicone oil, vaseline, petroleum wax and liquid paraffin The term "silicone oil" means any and all polyorganosiloxanes which are oily substances having the following unit in the structure:

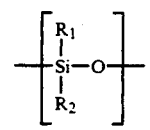

Typical polyorganosiloxanes are polydimethylsiloxane ($R_1$ and $R_2$ methyl) and polymethylphenylsiloxane ($R_1$ and $R_2$ are methyl and phenyl, respectively).

The petroleum wax is a petroleum refinery product specified in JIS K 2235 and includes paraffin wax, microcrystalline wax, petrolatum, etc. Particularly, petrolatum J.P. (Japanese Pharmacopoeia) is a highly purified product from petrolatum and includes white petrolatum and yellow petrolatum (soft paraffin).

The liquid paraffin is a petroleum fraction as specified in JIS K 2231 and is further classified by viscosity and so on.

The water-repellent organic compound can be used in an amount selected from within the range of 1 to 99 weight % based on the combined weight of phenol derivative (I) and water-repellent organic compound.

The combined amount of phenol derivative (I) and water repellent organic compound in the antifouling paint or fishnet dip according to this invention is generally 0.5 to 80 weight % and preferably about 1 to 50 weight %. In these compositions, too, other known ingredients can be incorporated as mentioned above and the manufacturing conditions for such composition may also be chosen from among the known techniques.

The following examples are intended to illustrate the invention in further detail and should by no means be construed as delimiting the scope of the invention.

EXAMPLES 1~9

In a test aqueduct having a total length of 100m and an average cross-sectional area of 0.1m², and running sea water at a rate of 400.1 per hour, antifouling effect of the present composition was examined.

That is, a series of test liquids were prepared by mixing each 10 kg of sea water and each 8 g of the phenol derivative shown in Table 1, respectively. In each test, the test liquid was drop-wise added at the entrance of said aqueduct to the running sea water in 8 hours a day. The same test was repeated every day for 10 days. 5 test plates (hard vinyl chloride plates, 100×300×3.2 mm) were placed in different positions in that aqueduct and after 10 days test period, the total wet weight of aquatic life collected from these test plates was measured. As a control, pure sea water containing no phenol derivative was added in place of the test liquid, which was shown as Comparative Example 1. Test results were shown in Table 1.

TABLE 1

| Example | phenol derivative | | | | | | total weight of adhered aquatic life(g) | | | | |
| --- | --- | --- | --- | --- | --- | --- | --- | --- | --- | --- | --- |
| | R | $X_1$ | $X_2$ | $X_3$ | $X_4$ | $X_5$ | A | B | C | D | E |
| 1 | $CH_3(CH_2)_8-$ | OH | H | H | H | H | 0 | 0 | 0 | 0.01 | 0.03 |
| 2 | $CH_3(CH_2)_8-$ | H | OH | H | H | H | 0 | 0 | 0 | 0.01 | 0.03 |
| 3 | $CH_3(CH_2)_8-$ | H | H | OH | H | H | 0 | 0 | 0 | 0 | 0.01 |
| 4 | $CH_3(CH_2)_8-$ | H | OH | H | OH | H | 0 | 0 | 0.02 | 0.03 | 0.1 |
| 5 | $CH_3(CH_2)_{16}-$ | H | OH | OH | OH | H | 0 | 0 | 0.01 | 0.03 | 0.1 |
| 6 | $CH_3(CH_3)_{20}-$ | $OCH_3$ | H | OH | H | $OCH_3$ | 0 | 0 | 0.02 | 0.03 | 0.1 |

TABLE 1-continued

| Example | phenol derivative | | | | | | total weight of adhered aquatic life(g) | | | | |
|---|---|---|---|---|---|---|---|---|---|---|---|
| | R | $X_1$ | $X_2$ | $X_3$ | $X_4$ | $X_5$ | A | B | C | D | E |
| 7 | | | nonyl phenol | | | | 0 | 0 | 0 | 0 | 0.01 |
| Comp. Ex. 1 | | | seawater containing no phenol derivative | | | | 6.0 | 5.0 | 2.5 | 2.0 | 1.5 |

Test plates were placed at the following positions:
A : entrance of aqueduct
B : 10 m behind the aqueduct entrance
C : 25 m behind the aqueduct entrance
D : 50 m behind the aqueduct entrance
E : 100 m behind the aqueduct entrance (aqueduct exit) and immersed in the running sea water.

In Comparative Example 1, both slime and small sized hard-shell mussels were observed at the test place surfaces, and however, in each example, only slimes were observed.

Examples 8~15 and Comparative Examples 2 and 3

Placing the indicated amounts of phenol derivatives and other ingredients shown in Table 2 in SG mil and effecting dispersion with glass beads, various antifouling paints were prepared.

On to a test steel plate (100×300 mm size) previously coated with a commercialized anticorrosive paint, each of the abovementioned antifouling paint was applied so as to give a dry film thickness of 60~80μ, and dried for 1 day. Thus obtained test plate was immersed (1 m depth) in sea water at the Aioi bay, Tamano shi, Okayama-ken, Japan, for 24 months and the antifouling effects were examined time to time. In Comparative Example 3, no antifouling paint was applied. The test results are shown in Table 3.

TABLE 3

| Immersion period Example | surface area(%) adhered noxious aquatic life | | | | |
|---|---|---|---|---|---|
| | 6 months | 12 months | 16 months | 20 months | 24 months |
| 8 | 0 | 0 | 0 | 0 | 5 |
| 9 | 0 | 0 | 0 | 0 | 5 |
| 10 | 0 | 0 | 0 | 5 | 10 |
| 11 | 0 | 0 | 0 | 5 | 10 |
| 12 | 0 | 0 | 0 | 5 | 10 |
| 13 | 0 | 0 | 0 | 5 | 10 |
| 14 | 0 | 0 | 0 | 5 | 10 |
| 15 | 0 | 0 | 0 | 0 | 5 |
| Comp. Ex. | | | | | |
| 2 | 0 | 0 | 0 | 0 | 20 |
| 3 | 50 | 80 | 100 | 100 | 100 |

EXAMPLE 16~25

A series of fish-net antifouling compositions were prepared by mixing and dispersing mixtures of alkyl phenol compounds and other materials shown in Table 4 in a high speed homodisper, respectively.

Test net (unknotted 60 twisted yarn, 6 knots, 20×30 cm) was dipped in the test composition and dried in air for 2 days.

Then the test net was immersed in 1 m depth in sea water at the Aioi bay, Tamano-shi, Okayama-ken, Japan, and antifouling effect was examined In comparative Example 4, tributyl tin methacrylate copolymer known as an organic tin, fish-net, antifouling agent was used and in Comparative Example 5, untreated fish net was used as a control.

Test results are shown in Table 5.

TABLE 2

| | Example | | | | | | | | | | Comp. Ex. |
|---|---|---|---|---|---|---|---|---|---|---|---|
| | 8 | 9 | 10 | 11 | | 12 | | 13 | 14 | 15 | 2 |
| phenol derivative of Example 1 | 20 | | | | 10 | 10 | | | | | |
| phenol derivative of Example 3 | | 20 | | | | 5 | | | | | |
| phenol derivative of Example 4 | | | 20 | | 10 | | | 5 | | | |
| phenol derivative of Example 5 | | | | 20 | | | | | 10 | | |
| phenol derivative of Example 7 | | | | | | | | | | 20 | |
| Ralolex MP-45 (*1) | 25 | 25 | 25 | 25 | 25 | 25 | 25 | | | 25 | 25 |
| WW rosin | 25 | 25 | 25 | 25 | 25 | 25 | 25 | | | | 25 |
| cuprous oxide | | | | | | | 15 | | | | 30 |
| fluid paraffin | | | | | | | | | | 5 | |
| KE 45-TS (*2) | | | | | | | | 70 | 55 | 50 | |
| SH-510 oil (*3) | | | | | | | | | 10 | 5 | |
| Haloflex 202 (*4) | | | | | | | | | 70 | | |
| dioctyl phthalate | 1 | 1 | 1 | 1 | 1 | 1 | 1 | | | | 1 |
| colloidal silica | 1 | 1 | 1 | 1 | 1 | 1 | 1 | | | | 1 |
| xylene | 20 | 20 | 20 | 20 | 20 | 20 | 20 | 20 | 30 | 20 | 15 |
| methyl isobutyl ketone | 8 | 8 | 8 | 8 | 8 | 8 | 8 | | | | 3 |
| water | | | | | | | | | 20 | | |
| Total | 100 | 100 | 100 | 100 | 100 | 100 | 100 | 100 | 100 | 100 | 100 |

(*1) Ralolex MP-45
vinyl chloride-vinyl isopropyl ether copolymer manufactured by BASF
(*2) KE 45-TS
one liquid type room temperature curing silicon rubber manufactured by Shinetsu Kagaku.
(*3) SH-510 oil
methyl phenyl silicon oil, manufactured by Toray Silicon.
(*4) Haloflex 202
aqueous vinyl acryl copolymer latex manufactured by Imperial Chem. Ind. Ltd.

Antifouling Composition used in Comparative Example 4:

| | |
|---|---|
| tributyl tin methacrylate/methyl methacrylate/ 2-ethyl hexyl acrylate copolymer (weight ratio of 60/32/8) | 30 parts |
| xylene | 70 parts |

TABLE 4

| Example | 16 | 17 | 18 | 19 | 20 | 21 | 22 | 23 | 24 | 25 |
|---|---|---|---|---|---|---|---|---|---|---|
| nonyl phenol (*5) | 30 | | | | 15 | | | | 7 | |
| p-nonyl phenol (*6) | | 30 | | | | 15 | | | | 5 |
| dodecyl phenol (*7) | | | 30 | | | | 15 | | | 5 |
| commercial p-t-octyl phenol (*8) | | | | 30 | | | | 15 | 7 | |
| Microwax (*9) | | | | | 15 | | | | | 5 |
| petrolatum (*10) | | | | | | 15 | | 15 | 10 | 10 |
| SH-510 oil (*3) | | | | | | | 15 | | | |
| fluid parrafin (*11) | | | | | | | | | 6 | 5 |
| xylene | 70 | 70 | 70 | 70 | 70 | 70 | 70 | 70 | 70 | 70 |
| | 100 | 100 | 100 | 100 | 100 | 100 | 100 | 100 | 100 | 100 |

(*5) commercial nonyl phenol
mixture of alkyl phenols, the alkyl being essentially of nonyl groups containing various isomers, manufactured by Sanyo Kasei Kogyo
(*6) commercial p-nonyl phenol
mixture of para-nonyl phenol and ortho-nonyl phenol (9:1), the nonyl containing various isomers, manufactured by Tokyo Kasei Kogyo
(*7) commercial dodecyl phenol
mixture of alkyl phenols, the alkyl being essentially of monododecyl phenol and containing various isomers, manufactured by Sanyo Kasei Kogyo
(*8) p-t-octyl phenol
containing 93% or more of p-octyl phenol, the octyl being 1,1,3,3-tetramethyl butyl manufactured by Tokyo Kasei Kogyo
(*9) Microwax
JIS K-2235 (petroleum wax) 150M equivalent
(*10) Petrolatum
JIS K-2335 (petroleum wax) No. 4 equivalent
(*11) fluid parrafin
JIS K-2231 ISOVG68 equivalent

TABLE 5

| Period | 1 month | 3 months | 6 months | 9 months | 12 months |
|---|---|---|---|---|---|
| Example | | | | | |
| 16 | 0 | 0 | 0 | 10 | 10 |
| 17 | 0 | 0 | 0 | 10 | 10 |
| 18 | 0 | 0 | 0 | 10 | 10 |
| 19 | 0 | 0 | 5 | 10 | 10 |
| 20 | 0 | 0 | 0 | 10 | 10 |
| 21 | 0 | 0 | 0 | 5 | 10 |
| 22 | 0 | 0 | 0 | 10 | 15 |
| 23 | 0 | 0 | 0 | 10 | 15 |
| 24 | 0 | 0 | 0 | 5 | 10 |
| 25 | 0 | 0 | 0 | 10 | 10 |
| Comp. Ex. | | | | | |
| 4 | 0 | 5 | 20 | 30 | 50 |
| 5 | 5 | 30 | 50 | 90 | 100 |

The indicated figure is net clogging %.

What is claimed is:

1. An antifouling composition for use in the control of noxious aquatic life comprising 5 to 80% by weight, based upon the total weight of the composition of one or more phenol derivatives of the formula:

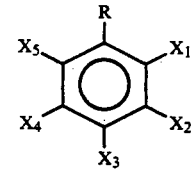

(I)

wherein R is a $C_{9-11}$ straight-chain or branched aliphatic saturated hydrocarbon residue; $X_1$–$X_5$ are the same or different and each is selected from the group consisting of hydrogen, hydroxy and methoxy providing that the case wherein all of $X_1$–$X_5$ are hydrogen is excluded and with the proviso that one of $X_1$–$X_5$ has to be —OH, and a water-repellent organic compound selected from the group consisting of silicone oil, vaseline, petroleum wax and liquid paraffin.

* * * * *